United States Patent [19]

Kouba et al.

[11] Patent Number: 4,613,707
[45] Date of Patent: Sep. 23, 1986

[54] HYDROGENATION USING COPPER ALUMINUM BORATE CATALYST

[75] Inventors: Jay K. Kouba, Downers Grove; Alex Zletz, Naperville, both of Ill.

[73] Assignee: Standard Oil Company (Indiana), Chicago, Ill.

[21] Appl. No.: 710,016

[22] Filed: Mar. 11, 1985

[51] Int. Cl.$^4$ .................. C07C 29/136; C07C 29/14
[52] U.S. Cl. ............................. 568/864; 568/881; 568/885
[58] Field of Search .................. 568/864, 881, 885

[56] References Cited

U.S. PATENT DOCUMENTS

| | | | |
|---|---|---|---|
| 2,009,948 | 7/1935 | Schmidt et al. | 568/881 |
| 2,040,944 | 5/1936 | Lazier | 568/864 |
| 2,456,633 | 12/1948 | Haensel | 568/885 |
| 3,856,702 | 12/1974 | McArthur | 252/432 |

*Primary Examiner*—J. E. Evans
*Attorney, Agent, or Firm*—William H. Magidson; William T. McClain; Ralph C. Medhurst

[57] ABSTRACT

The reduction of organic compounds to the corresponding hydroxy compounds which comprises contacting a suitable organic compound selected from the group consisting of organic carboxylic acid compounds, aldehydes and ketones with a reducing agent in the presence of a catalyst comprising at least one member selected from the group consisting of copper aluminum borate and zero valent copper on an aluminum borate support.

9 Claims, No Drawings

HYDROGENATION USING COPPER ALUMINUM BORATE CATALYST

This invention relates to the reduction of organic carboxylic compounds, aldehydes and ketones to the corresponding organic hydroxy compounds using a catalyst comprising at least one member selected from the group consisting of copper aluminum borate and zero valent copper on an aluminum borate support. More particularly, this invention relates to the reduction of dialkyl succinates to a composition comprising alkanols and butanediol using a catalyst comprising at least one member selected from the group consisting of copper aluminum borate and finely divided zero valent copper on an aluminum borate support.

Numerous patents disclose the reduction of carboxylic acid compounds (esters and carboxylic acids) to the corresponding alcohols. While numerous catalysts have been suggested for this reaction, there is a need for new catalysts, particularly new catalysts for the conversion of dialkyl esters of succinic acid to butanediol.

The general object of this invention is to provide a process of reducing organic compounds, preferably acids and esters to the corresponding alcohols. Other objects appear hereinafter.

For purposes of this invention the term "aluminum borate" is used in the generic sense to be inclusive of all crystalline aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, such as pure or neat copper aluminum borate, having the X-ray diffraction of $Cu_2Al_6B_4O_{17}$, copper zinc aluminum borate, aluminum borate/copper aluminum borate, copper aluminum borate/copper chromite, copper aluminum borate/alumina, etc.

We have now found that the objects of this invention can be attained by reducing organic carboxylic acid compounds to alcohols using a catalyst comprising at least one member selected from the group consisting of copper aluminum borate and zero valent copper on an aluminum borate support. This catalyst, particularly when it is combined with copper chromite, is useful in the conversion of dialkyl succinates to mixtures comprising alkanols corresponding to the alkyl group of the alkyl succinate, butanediol, tetrahydrofuran, and gamma-butyrolactone. As is well known, butanediol and tetrahydrofuran are both useful monomers for the production of polyesters (butanediol with terephthalic acid compounds) and polyethers (tetrahydrofuran). Gamma-butyrolactone is also a desirable solvent and precursor for the production of N-methyl pyrollidone, vinyl pyrollidone and polyvinyl pyrollidone.

The organic compounds suitable for use in this invention comprise organic carboxylic acid compounds (acids, anhydrides, and esters), aldehydes, ketones, etc. The carboxylic acid compounds (acids, esters and anhydrides), aldehydes and ketones are reduced to hydroxyl compounds. Suitable organic carboxylic acid compounds include aliphatic monocarboxylic acids having from 1–24 carbon atoms, such as formic acid, acetic acid, propionic acid, 2-ethylhexanoic acid, oleic acid, linoleic acid, linolenic acid, ricinoleic acid; polycarboxylic acids, such as malonic acid, succinic acid, maleic acid, fumaric acid, adipic acid, isophthalic acid, terephthalic acid, phthalic acid, 1,2,4-butane tricarboxylic acid, etc.; aliphatic esters of the aforesaid carboxylic acids, such as alkyl and alkenyl esters having from about 1–18 carbon atoms in the aliphatic groups, such as methyl acetate, ethyl propionate, vinyl acetate, cyclohexyl butyrate, dimethyl succinate, diethyl succinate, methylhydrogen succinate, ethyl hydrogen succinate, diallyl succinate, dioleyl succinate, diethyl terephthalate, etc.; aldehydes having from about 1–24 carbon atoms, such as formaldehyde acetaldehyde, butyraldehyde, etc., and ketones having from about 3–24 carbon atoms, such as acetone, methylethyl ketone, 12-tetracosanone, etc. As indicated above, the preferred organic compounds useful in this invention comprise dialkyl esters of succinic acid since the reduction products comprise 1,4-butanediol, tetrahydrofuran and gamma-butyrolactone which are difficult to produce but are commercially significant.

The catalysts useful in this invention comprise at least one member selected from the group consisting of copper aluminum borate and zero valent copper on a support comprising aluminum borate. While these catalysts can be prepared by any method (e.g., by vapor phase deposition of metallic copper on an aluminum borate support) the preferred catalysts are copper aluminum borate and reduction products thereof produced by the reduction of copper in crystalline copper aluminum borate. The preferred copper aluminum borates are disclosed and claimed in commonly assigned application Ser. No. 709,790 filed on even date in the name of Zletz, which is hereby incorporated by reference. The preferred zero valent copper on aluminum borate support is disclosed and claimed in commonly assigned application Ser. No. 710,015 filed on even date in the name of Zletz, which is hereby incorporated by reference.

If neat copper aluminum borate having the empirical formula $Cu_2Al_6B_4O_{17}$ is viewed as having the structure $3Al_2O_3.2CuO.2B_2O_3$, the reduction with CO or $H_2$ can be represented in its simplest terms as follows:

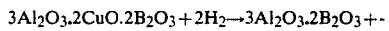

$$3Al_2O_3.2CuO.2B_2O_3 + 2H_2 \rightarrow 3Al_2O_3.2B_2O_3 + 2Cu + 2H_2O$$

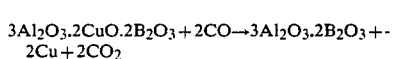

$$3Al_2O_3.2CuO.2B_2O_3 + 2CO \rightarrow 3Al_2O_3.2B_2O_3 + 2Cu + 2CO_2$$

X-ray diffraction patterns of the products indicate that the aluminum borate crystal has the formula $2Al_2O_3.B_2O_3$ and that part of the $B_2O_3$ in the original copper aluminum borate crystal has been driven off and/or is present in the amorphous state. Partial replacement of the copper in copper aluminum borate with other divalent metals does not interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB, aluminum borate and copper. The X-ray diffraction patterns in Table I show the significant lines for unreduced CuAB, substantially fully reduced CuAB (copper on aluminum borate), $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these, the relative intensities, 100 I/I$_0$, where I$_0$ is the intensity of the strongest line or peak, and d (obs.), the interplanar spacing in A, corresponding to the recorded lines, were calculated. In Table I, the relative intensities are given in terms of the symbols VVS=very very strong (over100), VS=very strong (80-100), S=strong (50-80), M=Medium (20-50), W=weak (10-20) and VW=very weak (<10).

TABLE I

| dA | Cu on AB | Cu AB | Uhlig Cu AB | Al$_4$B$_2$O$_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction line of the Al$_4$B$_2$O$_9$ or copper.

The significant X-ray diffraction lines for copper aluminum borate are set forth below in Table A.

TABLE A

| dA | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

The preferred copper aluminum borates have the formula Cu$_{2-x}$Al$_{6-y}$B$_4$O$_{17}$M$_m$M'$_n$M''$_y$ wherein M is a divalent metal, M' is a monovalent metal, m ranges from 0 to 0.8, n ranges from 0 to 1.6, X ranges from 0 to 0.8 and is equal to the sum of m+n/2, M'' is a trivalent metal and y range from 0 to 1.2.

Briefly, the preferred copper aluminum borates useful in this invention are preferably prepared by a three step procedure which comprises (1) combining a source of divalent copper, trivalent aluminum and boron in the form of the oxide or borate, (2) drying the composition to remove water or diluent if necessary and (3) calcining the composition at a temperature sufficiently high to form crystalline copper aluminum borate having an X-ray diffraction pattern of Cu$_2$Al$_6$B$_4$O$_{17}$.

While copper aluminum borates useful in this invention can be prepared by various techniques, it is generally preferred to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatized during the subsequent drying and/or calcination step. The presence of volatile components in preparation of copper aluminum borate, such as water, NH$_3$, acetate, etc., is advantageous in providing the copper aluminum borate with sufficient surface area and porosity for catalysis. Preferably, the catalyst has a surface area of at least 5 m$^2$/g. However, lower surface area copper aluminum borates can be used.

Accordingly, preferred sources of copper for use in this invention include copper nitrate, copper acetate, copper carbonate, copper borate, etc. since the nitrate, acetate and carbonate anions are destroyed during the drying or calcination step. Suitable sources of boron ion include boric acid, copper borate, aluminum borate, boron oxides and ammonium borate. The aluminum can be present in the form of alumina sols, aluminum nitrate, alumina, aluminum acetate, aluminum borate, etc. It is generally desirable to employ ammonium salts or ammonium hydroxide to increase the surface area and porosity of the copper aluminum borate. These components can be combined in an aqueous medium in approximately stoichiometric proportions to provide Cu$_2$Al$_6$B$_4$O$_{17}$. In some cases, it is desirable to have excess aluminum and borate present in the catalyst precursor in order to form a mixed copper aluminum borate/aluminum borate crystal.

If desired, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been successfully incorporated into copper aluminum borate crystals and, accordingly, X in the above formula can range from about 0.01 to 0.8, preferably about 0.05 to 0.50. Trivalent metal ions can appear as M'' in the above formula, e.g., Fe$^{+++}$. However, chromium forms a chromite and appears not to replace aluminum.

While it is generally preferred to produce neat copper aluminum borate or copper aluminum borate/aluminum borate catalysts, the partial replacement of aluminum with chromium in the preparation (about 5 to 25%) yields an excellent hydrogenation catalyst (copper aluminum borate/copper chromite).

If desired, non-volatile cations such as alkali metal (M' in the above formula) or alkaline earth metal cations can be present during the preparation of the copper aluminum borate.

In somewhat greater detail, the copper salt and boron compound are desirably dissolved in water together with a water soluble aluminum salt and/or alumina in the form of sols or powder. The composition is dried (e.g. at atmospheric pressure or under vacuum) and then calcined to a temperature of about 650° C. to 1000° C., preferably at least 750° C. for about 0.1 to 24 hours, typically in air. The higher the calcination temperature the shorter the calcination time. Calcination at about 680° C. for about 3 hours generally leads to about 20% crystallinity of copper aluminum borate, while calcination at about 845° C. for about 3 hours generally leads to about 80% crystallinity. Calcinations above about 800° C. tend to provide a blue-green crystalline material. Other things being equal, the higher the calcination temperature the lower the surface area and porosity of the copper aluminum borate. For example, copper aluminum borate calcined at 830° C. had a surface area of 19 $m^2/g$, pore volume of 0.1639 cc/g and an average pore radius of 293 Å, whereas the same material calcined at 925° C. had a surface area of 7 $m^2/g$, pore volume of 0.0402 cc/g and an average pore radius of 334 Å. Of course, the optimum calcination temperature is dependent on the particular composition calcined, the calcination time, the volatiles present during the preparation of the composition and the desired surface area and porosity.

The calcined copper aluminum borate can be used as a hydrogenation catalyst or treated with reducing gas, such as hydrogen or carbon monoxide at a temperature of from 150° C. to 1000° C. to convert same into catalysts having a surface area of at least 5 square meters per gram, comprising finely divided metallic copper on a support comprising aluminum borate. The higher the temperature of the reducing gas and the more effective the reducing gas, the lower the concentration of copper aluminum borate in the aluminum borate support. If the copper aluminum borate is used directly as a catalyst without pretreatment with a reducing gas, the copper aluminum borate can be converted into a catalyst having a surface area of at least 5 meters per gram, comprising finely divided copper on a support comprising aluminum borate by the reducing agent.

The organic compounds can be reduced under conventional conditions using the catalysts of this invention (copper aluminum borate and copper on aluminum borate supports). The reaction can be carried out on a continuous basis by passing a liquid stream or gaseous mixture and hydrogen through a catalyst bed or reduction can be carried out batchwise. Generally, organic carboxylic acid compositions containing about 1% by weight or more unesterified carboxylic acid or anhydride components are preferably reduced by passing the composition through a catalyst bed or by using an alcoholic solvent or diluent ($C_1$ to $C_{12}$ alkanol) to overcome any inhibitory effects of the unesterified carboxyl groups. Reduction can be carried out at a temperature of from 100° to 300° C., preferably about 150° to 300° C. for dialkyl succinates. The process can be carried out at a pressure of from about 1000 to 5000 psig.

EXAMPLE I

This Example illustrates that substantially fully reduced copper aluminum borate (finely divided copper on aluminum borate support) has a different X-ray diffraction pattern from its unreduced precursors.

A hot solution of 23.16 g boric acid in 240 ml distilled water was added to 297.16 g of alumina sol (9.73 wt.% $Al_2O_3$ by calcining at 500° C.) in a Waring blender. To 37.35 g of copper acetate were added 100 ml distilled water and 30 ml conc. NH4OH. This brought nearly all of the solid into solution and was added to the blender. An additional 30 ml conc. NH4OH was added to the small amount of remaining solid which was then transferred to the blender. One hundred ml distilled water was used to transfer all remaining materials to the blender. After each of these additions the mixture was thoroughly mixed and the final product was spread out to dry for eight days before drying in a vacuum oven to 90° C. This product (II-1) was then calcined at 820° C. for three hours and had a surface area of 54 $m^2/g$, a pore volume of 0.2663 cc/g and an average pore radius of 92 Å.

The copper aluminum borate was loaded into a ¾" quartz reactor tube and placed in a Lindberg furnace. The reactor system was equipped with regulators for controlling nitrogen flow and a syringe pump for controlling liquid flows. The liquid was vaporized in a "preheat" section of the reactor and mixed with nitrogen before contacting the catalyst. The reactor effluent was fed into a 10 port gas sampling valve through heated lines. On a signal from the gas chromatograph, an 0.1 cc sample of the reactor effluent was injected into a Perkin-Elmer Sigma 2B Gas Chromatograph. A series of columns and splitters allowed the analysis of both inorganic gases (TC detector) and organics (FID) simultaneously.

Initially, a 4.7 cc bed of the catalyst was used and mesityl oxide was injected into the system with 5% oxygen using a nitrogen diluent gas at a temperature of 200° C. Over a period of about 4 to 5 hours the temperature was raised gradually to 500° C. when the catalyst coked up badly. The catalyst was decoked with 5% oxygen in nitrogen for about 1 hour. Paraxylene was then substituted for the mesityl oxide and was fed to the reactor. Over a period of 3 to 4 hours the temperature was increased from about 200° to 500° C. without oxidation taking place. Then para-cymene was used to replace the paraxylene and the temperature was increased to 600° C. over a period of several hours using a Liquid Space Velocity (LSV) 0.1 ($Hr^{-1}$) resulting in a 92% conversion of the paracymene yielding a selectivity of 10% to para methyl-alpha methylstyrene. As soon as oxygen was deleted from the feed, conversion dropped to about 83% and selectivity to paramethyl alpha methylstyrene increased to 90%.

The next day the reactor was started up again except that paraethyltoluene was fed to the reactor with nitrogen for 4 hours at 600° C. using a 0.1 LSV ($H^{-1}$) and 1000 GSV ($Hr^{-1}$). Periodic samples indicated that the conversion ranged from about 49 to 53.9% with selectivity ranging from 87 to 92% to paravinyltoluene. The next day the paraethyltoluene run was repeated over a period of 8 hours except using a 0.50 LSV. The percent conversion dropped to about 22 to 27% and the selectivity increased to about 92 to 96%. The next day the run was repeated with essentially the same results. The next day ethylbenzene was used in place of the paraethyltoluene using 0.5 LSV ($Hr^{-1}$) and a 600 CSV ($Hr^{-1}$) resulting in percent conversion ranging from about 19 to 38% with selectivity of from 64 to 84% to styrene. During this period the process was permitted to run overnight for 16 hours. The used copper colored catalyst is described below as I-2.

A fresh sample of copper aluminum borate (I-1) was used to replace I-2 and a 3.3 cc catalyst bed was prepared. Cumene and nitrogen diluent was fed to the catalyst for several days varying the conditions as set forth below in Table II. The run numbers refer to various sampling points.

TABLE II

| Sample No. | Temp. (°C.) | LSV (Hr-1) | GSV (Hr-1) | Conversion | Selectivity | Time After Startup |
|---|---|---|---|---|---|---|
| 1 | 600 | 0.50 | 740 | 70.7 | 82.9 | |
| 2 | 650 | 0.96 | 450 | 77.9 | 67.7 | |
| 3 | 550 | 0.14 | 450 | 40.4 | 90.0 | |
| 4 | 650 | 0.14 | 2100 | 91.1 | 75.2 | |
| 5 | 650 | 0.96 | 2100 | 77.4 | 74.2 | |
| 6 | 600 | 0.50 | 740 | 56.9 | 84.3 | |
| 7 | 550 | 0.14 | 2300 | 27.7 | 81.6 | |
| 8 | 550 | 0.96 | 2300 | 9.9 | 83.4 | |
| 9 | 550 | 0.96 | 500 | 19.8 | 74.5 | |
| 10 | 650 | 0.14 | 400 | 80.0 | 68.9 | |
| 11 | 600 | 0.50 | 740 | 56.5 | 85.1 | |
| 12 | | | | 42.9 | 90.0 | 9 hrs. |
| 12A | | | | 44.8 | 89.7 | 24 hrs. |
| 13 | 600 | 0.50 | 740 | 54.6 | 84.7 | |
| 14 | 600 | 1.37 | 700 | 41.3 | 82.6 | |
| 15 | 675 | 0.50 | 700 | 79.5 | 65.4 | |
| 16 | 525 | 0.50 | 700 | 10.2 | 93.7 | |
| 17 | 600 | 0.50 | 740 | 51.6 | 86.3 | |
| 18 | 600 | 0.10 | 700 | 75.9 | 87.3 | |
| 19 | 600 | 0.50 | 3100 | | | Data lost due to valve failure |
| 20 | 600 | 0.50 | 400 | 64.9 | 75.8 | |
| 21 | 600 | 0.50 | 740 | 51.1 | 84.9 | |
| 22 | | | | 38.1 | 89.8 | 32 hrs. |
| 23 | | | | 39.9 | 89.6 | 48 hrs. |
| 24 | | | | 37.2 | 89.5 | 53 hrs. |
| 25 | | | | 36.8 | 89.0 | 73 hrs. |
| 26 | | | | 36.9 | 88.9 | 74 hrs. |

This procedure was carried out for approximately 6 weeks varying the conditions. The copper colored catalyst at this point (I-3) was removed from the reactor and comprised finely divided copper on aluminum borate. Each of the catalyst samples, copper aluminum borate (I-1) and finely divided copper on aluminum borate (I-2 and I-3), were run under the X-ray diffraction conditions referred to above. The strongest line for the copper aluminum borate was 5.29 and the strongest line for the copper on aluminum borate was 2.09 or 2.08 (the copper metal line). In order to make the data more readily comparable, 5.28 and 5.29 were selected as 100%. The X-ray diffraction patterns of these materials is set forth below in Table III.

TABLE III

| dA | I-1 I/I$_o$ | I-2 I/I$_o$ | I-3 I/I$_o$ |
|---|---|---|---|
| 7.46 | 13 | | |
| 5.29 | 100 | 100 | |
| 5.28 | | | 100 |
| 4.99 | 62 | | |
| 4.93 | | 24 | |
| 4.91 | | | 19 |
| 3.73 | 17 | | |
| 3.64 | 9 | | |
| 3.59 | | 12 | 19 |
| 3.35 | | 12 | |
| 3.34 | 14 | | 26 |
| 2.96 | 11 | | |
| 2.84 | 14 | | |
| 2.78 | | 5 | 8 |
| 2.645* | 77 | | |
| 2.64 | | 44 | 38 |
| 2.61 | 20 | | |
| 2.50 | 21 | | |
| 2.46 | | 26 | 42 |
| 2.26 | 30 | | |
| 2.23 | | 12 | |
| 2.22 | | | 17 |
| 2.16 | 39 | | |
| 2.13 | | 47 | 40 |
| 2.09 | | 586 | |
| 2.08 | | | 563 |
| 2.07 | 34 | | |
| 1.98 | 27 | | |
| 1.97 | | 7 | |
| 1.96 | | | 10 |
| 1.91 | | 7 | 8 |
| 1.86 | 19 | | |
| 1.82 | 24 | | |
| 1.81 | | 222 | 217 |
| 1.76 | 9 | | |
| 1.67 | 31 | | |
| 1.66 | | 16 | 19 |
| 1.59 | 11 | | |
| 1.56 | 10 | | |
| 1.55 | | 15 | 18 |

*2.61 was a shoulder on 2.645

EXAMPLE II

A hot solution of 23.73 g of boric acid in 250 ml distilled water was added to 307.1 g of alumina sol (9.56 wt.% solids by calcining at 500° C.) in a blender while mixing. To this were added 46.30 g copper nitrate [Cu(NO$_3$)$_2$.3H$_2$O] dissolved in 50 ml distilled water. Then 60 ml conc. ammonium hydroxide were added and the resulting mixture was blended until uniform and smooth. The product was spread out to dry overnight and was then dried in a vacuum oven at 130° C. A portion of the vaccum-dried product was calcined at 830° C. for about three hours. This product is estimated to contain 1.5 wt.% excess alumina.

EXAMPLE III

A hot solution of 26.32 g boric acid in 260 ml distilled water was added to 306.56 g of alumina sol (9.56 wt.% solids) in a blender while mixing. To this was added a solution of 51.40 g copper nitrate [Cu(NO$_3$)$_2$.3H$_2$O] and 15.77 g chrominum acetate [Cr(C$_2$H$_3$O$_2$)$_3$.H$_2$O] in 110 ml distilled water. After thorough mixing, 61 ml of conc. ammonium hydroxide were added. Mixing was continued until a smooth and uniform product was obtained. It was spread out to dry for five days and then dried in a vacuum oven at 130° C. A portion of the vacuum-dried product was calcined at 765° C. (III-1). Assuming no chrominum is incorporated in the copper aluminum borate structure and the chromium is completely converted to copper chromite, the final preparation contains 11.2 wt.% CuCr$_2$O$_4$. X-ray diffraction indicated that all chromium was converted to copper chromite.

EXAMPLE IV

These preparations were performed as in Example III except that stoichiometric amounts of ingredients for Cu$_2$Al$_6$B$_4$O$_{17}$ and 11.2% and 22.4% by wt CuCr$_2$O$_4$ were provided. Thus, for the 22.4 wt.% copper chromite the quantities used were: 299.18 g alumina sol (9.73 wt.% solids by calcining at 500° C.), 23.53 g boric acid dissolved in 250 ml distilled water, 62.82 g copper nitrate dissolved in 60 ml distilled water, 35.42 g chromium acetate dissolved in 90 ml distilled water and 70 ml conc. ammonium hydroxide. The product was air-dried overnight and vacuum-dried at 110° C. A portion of this product was calcined in two steps. In the first step, the product was heated to 410° C. and then was heated to 780° C. for three hours in the second step (IV-1). The product with 11.2 wt.% $CuCr_2O_4$ was also calcined in this manner (IV-2).

EXAMPLE V

In this preparation, aluminum nitrate was used instead of alumina sol. It was performed in a 1000 ml beaker placed on a hot plate and provided with an electric driven paddle stirrer. Aluminum nitrate [Al(NO$_3$)$_3$.9H$_2$O], 225.10 g, was dissolved in 475 ml distilled water. To this solution were added 24.73 g boric acid, 59.99 g copper nitrate [Cu(NO$_3$)$_2$.3H$_2$O], and 38.67 g chromium nitrate [Cr(NO$_3$)$_3$.9H$_2$O]. The pH of this black solution was 1.3 when dropwise addition of conc. ammonium hydroxide was started. After 39 minutes, 80 ml had been added and the pH was 2.8. Addition was continued with a 1 to 1 solution of conc. NH$_4$OH in distilled water. After 70 minutes, 87.5 ml had been added, the pH was 3.7, and the product was a stiff gel. The beaker was left covered for 24 hours, the contents were spread out to dry for two days and then was vacuum-dried at 105° C. A portion of this product was calcined at 430° C. (V-1). A portion was next calcined at 730° C. for three hours (V-2) and another portion was calcined at 770° C. for three hours (V-3).

EXAMPLE VI

This example illustrates hydrogenation of diethylsuccinate to obtain butanediol using either copper aluminum borate as the hydrogenation catalyst or copper aluminum borate/copper chromite. Hydrogenations were carried out in a 1-liter 316 SS autoclave containing 150 grams diethylsuccinate, 450 grams ethanol and powered catalyst. Hydrogen was admitted to the reactor to maintain a pressure of 2000 psig. The temperature was maintained at 200° C. The results are set forth in Table IV.

TABLE IV

| Catalyst | Weight of Catalyst (grams) | Hydrogenation Rate (mole fraction/min.) |
|---|---|---|
| Example II | 9.0 | $0.79 \times 10^{-3}$ |
| Example III-1 | 8.2 | $1.58 \times 10^{-3}$ |

EXAMPLE VII

This example illustrates the conversion of dimethylsuccinate to butanediol using a copper chromite commercial hydrogenation catalyst and copper aluminum borate catalysts containing the indicated concentrations of copper chromite. The reactions were carried out by charging the reactor with 40 grams dimethylsuccinate, 120 grams methanol and 4 grams of powdered catalyst. The hydrogenation was carried out at 200° C., 1800 psig for 6.5 hours. The results are set forth below in Table V.

TABLE V

| Catalyst | % Copper Chromite | % DMS[2] Conversion | Selectivity (%) | | | |
|---|---|---|---|---|---|---|
| | | | GBL | BDO | MHB | MHBS |
| Strem - barium promoted copper chromite 29-041 | 100% | 38.7 | 19.0 | 57.4 | 15.8 | 7.8 |
| Example IV-1 | 22% | 34.0 | 22.6 | 52.6 | 18.3 | 6.5 |
| Example IV-2 | 11% | 28.4 | 39.8 | 40.6 | 14.8 | 4.8 |
| Example V-2 | 15.6% | 21.0 | 50.8 | 7.1 | 42.1 | Low |
| Example V-3 | 15.6% | 18.0 | 50.7 | 30.9 | 18.4 | Low |

[2]DMS = dimethylsuccinate
GBL = gamma-butyrolactone
BDO = 1,4-butanediol
MHB = methyl-4-hydroxybutyrate
MHBS = methyl(4-hydroxybutyl)succinate

What is claimed is:

1. The reduction of organic compounds to the corresponding hydroxy compounds which comprises contacting a suitable organic compound selected from the group consisting of organic carboxylic acid compounds, aldehydes and ketones with a reducing agent in the presence of a catalyst comprising at least one member selected from the group consisting of copper aluminum borate and zero valent copper on a crystalline $Al_4B_2O_9$ support wherein said catalyst is formed by the reduction of crystalline copper aluminum borate having the significant x-ray diffraction lines set forth in Table A.

2. The process of claim 1, wherein said catalyst comprises a mixture of copper chromite and at least one member selected from the group consisting of copper aluminum borate and zero valent copper on crystalline $Al_4B_2O_9$.

3. The process of claim 1, wherein the reducing agent comprises hydrogen.

4. The process of reducing an organic carboxylic acid compound which comprises contacting a composition comprising an organic carboxylic acid ester with a reducing agent in the presence of a catalyst comprising at least one member selected from the group consisting of copper aluminum borate and zero valent copper on a crystalline $Al_4B_2O_9$ support wherein said catalyst is formed by the reduction of crystalline copper aluminum borate having the significant x-ray diffraction lines set forth in Table A.

5. The process of claim 4, wherein the catalyst comprises a mixture of copper chromite and at least one member selected from the group consisting of copper aluminum borate and zero valent copper on an crystalline $Al_4B_2O_9$.

6. The process of claim 4, wherein said organic carboxylic acid compound comprises dialkyl succinates.

7. The process of claim 6, wherein the alkyl group comprises at least one member selected from the group consisting of methyl and ethyl.

8. The process of claim 4, wherein said catalyst comprises copper aluminum borate.

9. The process of claim 4, wherein said catalyst comprises zero valent copper on an crystalline $Al_4B_2O_9$.

* * * * *